(12) United States Patent
Jones

(10) Patent No.: US 7,220,267 B2
(45) Date of Patent: *May 22, 2007

(54) SURGICAL NEEDLE HOLDER

(76) Inventor: Michael Harold Jones, M.H. Jones Laboratory, 248, Old Bath Road, Cheltenham, Gloucestershire, GL53 9EQ (GB)

( * ) Notice: Subject to any disclaimer, the term of this patent is extended or adjusted under 35 U.S.C. 154(b) by 576 days.

This patent is subject to a terminal disclaimer.

(21) Appl. No.: 10/601,579

(22) Filed: Jun. 24, 2003

(65) Prior Publication Data

US 2004/0122372 A1 Jun. 24, 2004

(30) Foreign Application Priority Data

Jun. 25, 2002 (GB) .................................. 0214635.5

(51) Int. Cl.
*A61B 17/04* (2006.01)
(52) U.S. Cl. ...................................................... 606/145
(58) Field of Classification Search .................. 606/44, 606/144, 145, 147, 184–189, 222, 223; 604/264, 604/21
See application file for complete search history.

(56) References Cited

U.S. PATENT DOCUMENTS 3,799,168 A * 3/1974 Peters .......................... 606/45
5,433,722 A * 7/1995 Sharpe et al. ................ 606/148
5,628,757 A * 5/1997 Hasson ........................ 606/148
6,440,108 B1 * 8/2002 Jones .......................... 604/264
6,926,730 B1 * 8/2005 Nguyen et al. ............. 606/213

FOREIGN PATENT DOCUMENTS

WO     WO 99/35985 A     7/1999

OTHER PUBLICATIONS

Abstract of GB 2 350 064 A.

* cited by examiner

*Primary Examiner*—Eduardo C. Robert
*Assistant Examiner*—Michael J. Araj
(74) *Attorney, Agent, or Firm*—Birch, Stewart Kolasch & Birch, LLP

(57) ABSTRACT

A holder for a surgical needle provided with a safety release mechanism which is designed so that when the device is not in use either by way of a deliberate action on the part of the operator, or where for example the device is accidentally dropped, the needle automatically retracts within the holder to prevent injury to the operator or other persons.

5 Claims, 1 Drawing Sheet

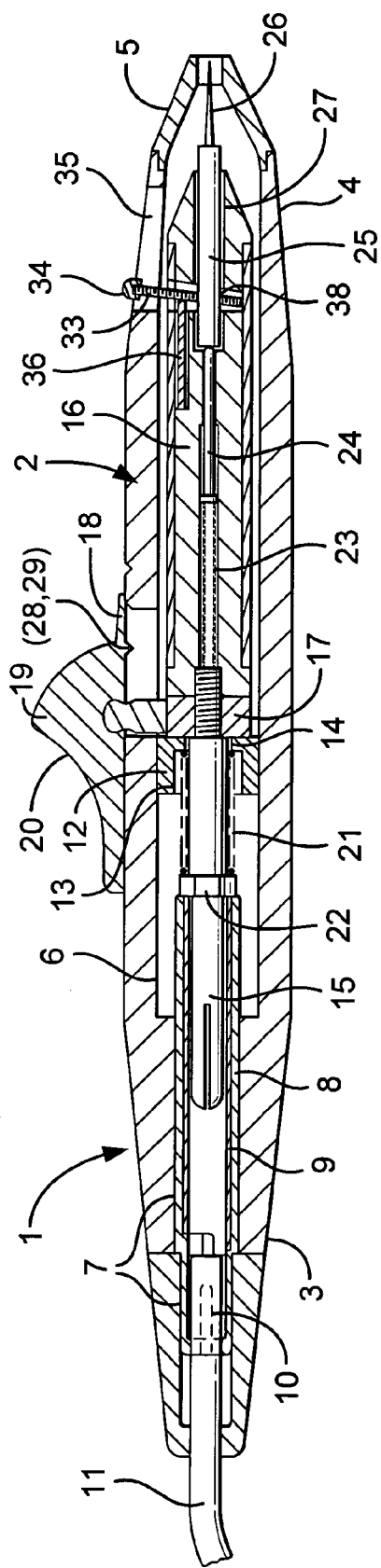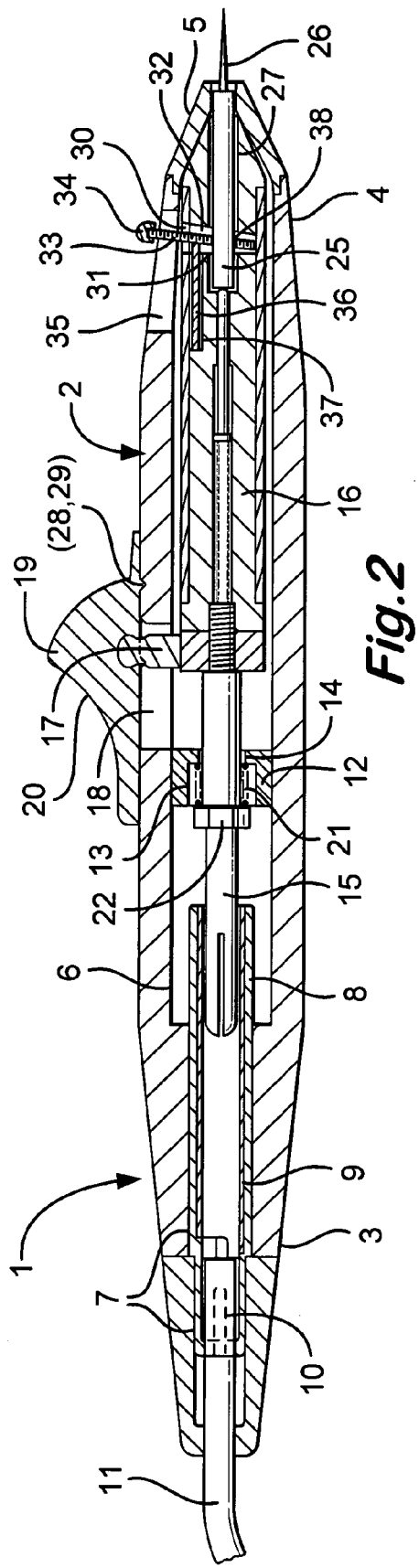

SURGICAL NEEDLE HOLDER

FIELD OF THE INVENTION

The present invention relates to a holder for a surgical needle and particularly to a holder for a surgical needle provided with a safety release mechanism for the surgical needle so that when the device is not in use either by way of a deliberate action on the part of the operator or where for example the device is accidentally dropped, the needle automatically retracts within the holder to prevent injury to the operator or other persons.

BACKGROUND OF THE INVENTION

Surgical needles mounted in specially designed holders are used in medical practice in the areas of, for example, hair removal by electrolysis such as ophthalmic treatment, and certain aspects of cosmetic surgery.

Handling and disposal is important in the use of surgical needles both from the point of view of the health of the patient and the user.

There are various types of surgical needle holders in use at the present time. An example of one such needle is to be found in the applicant's existing patent GB 2,350,064 which is provided with a novel releasable locking means for locking the shank of the needle within the body of the device with the needle protruding from the operating end of the device ready for use.

New surgical needles are provided with protective sheaths which are removed once installed in the needle holder and it is therefore paramountly important that thereafter the needle does cause injury either to the operator, the patient or other persons by being for example improperly used or accidentally dropped. Since the needle is unprotected such injury can occur when for example the device is temporarily put to one side during a surgical procedure or disposed of in a reckless manner.

SUMMARY OF THE INVENTION

It is an object of the present invention to overcome the disadvantages of prior surgical needle holders as briefly explained above.

According to invention there is provided a surgical needle holder comprising an electrically insulated housing, an insulated electrically-conducting support body within the housing for mounting a surgical needle, and an actuating mechanism for the support body including an operating knob on the housing moveable by an operator from a first position to cause the mechanism to move the support body and withdraw the surgical needle within the housing and a second position to move the needle to an operating position external to the housing, and means biasing the actuating mechanism to said first position so that when the operator releases the operating knob the needle is automatically withdrawn within the housing of the needle holder.

Preferably the actuating mechanism is in the form a moveable plunger carrying the surgical needle and mounted within the holder, and spring means acting to bias the plunger when under tension as the plunger is moved to the forward position thereby constraining the plunger to return the needle to the withdrawn position when the tensioning force is removed upon release of the operating knob by the operator.

BRIEF DESCRIPTION OF THE DRAWINGS

Other features and advantages of the present invention will become apparent from the following description of a preferred embodiment thereof taken with reference to the accompanying drawings wherein:

FIG. 1 is a cross-section of the surgical needle holder showing the position of the surgical needle in a retracted position; and FIG. 2 is a cross-section of the surgical needle holder as shown in FIG. 1 illustrating the position of the surgical needle in an operating position.

BEST MODES OF CARRYING OUT THE INVENTION

The surgical needle holder (1) shown in FIGS. 1 and 2 comprises an outer generally cylindrical hollow plastic body portion (2) having a tapered tail end (3) and a tapered forward end (4) provided with a disposable sterile, cone-shaped nozzle (5).

The generally cylindrical body portion (2) of the needle holder (1) is provided with an inner cylindrical bore (6) extending to the cone-shaped nozzle (5).

An inner bore (7) of smaller diameter than the bore (6) is formed in the tapered tail end (3) of the surgical needle holder (1). The bores (6) and (7) share the same axis which lies along the longitudinal axis of the holder (1).

A hollow plastic insulation tube (8) is fitted into the bore (7) and extends from the bore (7) into the bore (6) of the generally cylindrical body portion (2) of the surgical needle holder (1). The interior of the tube (8) is fitted with a sleeve (9) of electrically conducting material.

The insulation tube (8) houses an electrical connector (10) for connecting the needle holder to an R F generator (not shown) through lead wires (11).

A collar (12) is mounted in a fixed position in the cylindrical bore (6), the collar (12) having a first bore portion (13) and a second bore portion (14) of smaller diameter than the first bore portion (13).

A cylindrical shaft (15) made of brass is mounted in the tube (8) for sliding contact with the inner sleeve (9) of the tube (8).

The cylindrical shaft (15) extends through the bore portions (13, 14) of the fixed collar (12) to connect with a cylindrical plunger shaft (16) moveable in the bore (6), one end of which is provided with a connecting arm (17) slidable in a longitudinally extending slot (18) formed in the body (2) of the holder (1).

The other end of the plunger shaft (16) is conically-formed for mating engagement with the inner surface of the conical nozzle (5).

The connecting arm (17) on the plunger shaft (16) is secured to an operating button (19) which is slidable along the outer surface of the body (2) of the holder (1) by finger pressure applied by an operator to the upper curved indent (20) of the button (19) to move the plunger shaft (16) from a maximum rearward retracted position as shown in FIG. 1 to a maximum forward position shown in FIG. 2 whereat the conical end of the plunger shaft (16) comes to rest against the inner conical surface of the conical nozzle (5).

A coiled spring (21) is mounted around a portion of the cylindrical shaft (15) and is held in position between a fixed abutment (22) on the shaft (15) and the base ledge wall of the first bore portion (13) in the collar (12) as shown more clearly in FIG. 1 in the relaxed position of the spring (21).

In this relaxed state of the spring (21), the abutment (22) rests against the forward end of the tube (8) with the plunger shaft (16) against the fixed collar (12) and the connecting arm (17) together with the button (19), at its maximum rearward position in the slot (18).

The central core of the plunger shaft (16) is provided with an axially-extending ejection spring (23) which engages a pin (24) bearing on the shank (25) of a surgical needle (26) mounted in a bore (27) extending axially of the plunger shaft (16) from its conical top as shown in FIGS. 1 and 2.

When the button (19) is pushed to its forward operating position as shown in FIG. 2 the coiled spring (21) is compressed between the abutment (22) and the collar (12) so providing a force tending to return the needle (26) to a withdrawn position within the body of the holder (1). Resistance to this movement is provided by finger pressure of the operator on the button (19) in addition to the added resistance provided by the engagement of a projection (28) on the button (19) with a corresponding notch (29) formed in the outer surface of the body portion (2) of the needle holder (1) as shown.

The force exerted by the coiled spring (21) under compression when the surgical needle (25) is in its projected position as shown in FIG. 2, is greater than those forces acting between the projection (28) when in engagement with the notch (29) without the application of finger pressure, so that when finger pressure is released the projection (28) and notch (29) disengage automatically and the needle (26) is brought safely behind the sterile front cone nozzle (5).

This safety feature has added importance should the needle holder (1) accidentally be dropped since the safety actuating mechanism in accordance with the invention will instantly retract the needle (26) so that it is behind the sterile front cone (5) and can not cause injury. In addition any time the needle holder (1) is not held correctly the needle (26) will be constrained to stay safely retracted.

The needle holder (1) as shown in the drawings is provided with a releasable locking means for locking the needle shank (25) in the bore (27) of the plunger shaft (16).

To this end the plunger shaft (17) is provided with a cylindrical cavity (30) having a vertical face (31) and opposing face (32) inclined thereto.

An electrically conducting cylindrical plate (33) having an insulated tab portion (34) occupies the cavity (30) with the tab portion (34) extending through a longitudinally extending slot (35) in the outer body (2) of the surgical needle holder (1).

The longitudinal extent of the slot (35) corresponds to that of the slot (18) so that the plate (33) with tab portion (34) moves in the slot (35) in the same manner and at the same time as the connecting arm (17) moves in the slot (18) during movements of the plunger shaft (16).

By reason of the opposing vertical and inclined faces (31, 32) of the cavity (30) the plate (33) is pivotally moveable from an upright position to a maximum forward inclined position as shown in the drawings and intermediate positions therebetween.

The plate (33) is urged to its maximum forward position as shown in the drawings by means of a coiled spring (36) housed in a groove (37) formed in the surface of the plunger shaft (16). The plate (33) has a central aperture (38) which when in its upright pivotable position its axis may be brought into alignment with the axis of the bore (27) to allow the shank of the needle (25) to be inserted into the bore (27) to its operating position.

The plate (33) is then released to its forward pivotal position by the urging of the spring (36) as shown in the drawings so that the shank of the needle (25) is gripped in the aperture (37) of the plate (33) and any effort to release the needle (26) by pulling it only serves to increase the gripping force.

Apart from the incorporation of the longitudinally extending slot (35) for the reason as explained above, the releasable locking means for the surgical needle as described forms no part of the present invention such being protected by and more fully disclosed in my patent GB 2,350,064 referred to above, and has only been included in this description for the purposes of a better understanding and comprehension of the invention.

The invention claimed is:

1. A surgical needle holder comprising:
an electrically-insulated housing,
an insulated electrically-conducting support body within the housing for mounting a surgical needle, and
an actuating mechanism for the support body including an operating knob on the housing moveable by an operator from a first position to cause the mechanism to move the support body and withdraw the surgical needle within the housing, and a second position to move the needle to an operating position external to the housing, and
means biasing the actuating mechanism to said first position so that when the operator releases the operating knob the needle is automatically withdrawn within the housing of the needle holder, wherein the actuating mechanism is in the form of a moveable plunger carrying the surgical needle and mounted within the holder, and spring means acting to bias the plunger when under tension as the plunger is moved to the forword position, thereby constraining the plunger to return the needle to the withdrawn position when the tensioning force is removed upon release of the operating knob.

2. The surgical needle holder as claimed in claim 1 wherein the plunger has an actuating arm extendinmg through a slot in the housing to engage the operating knob, said slot having a longitudinal-extent delimiting the forword and reverse movements of the plunger.

3. The surgical needle as claimed in claim 1 wherein the spring means is in the form of a coiled spring around an electrically conducting shaft attached to the plunger, the coiled spring being held between two statements one of which is fixed on the shaft, the other stationary, such that the coiled spring is compressed upon movement of the plunger to the forward position between the fixed abutments so providing the constraining force tending to return the plunger to its withdrawn position.

4. The surgical needle holder as claimed in claim 1 wherein the electrically-conducting shaft is slidable within a hollow tube, the hollow tube being sleeved with an electrically-conductive material connected to an electrical connector within the tail end of the housing.

5. The surgical needle holder as claimed in claim 1 wherein the plunger is provided with an axially-extending ejector pin bearing on the shank of the needle holder and a spring held under tension between the ejector pin and the electrically-conducting shaft such that when the surgical needle is released, the ejector pin propels the needle from the holder ready for installation of a new surgical needle.

* * * * *